(12) United States Patent
Lawrence et al.

(10) Patent No.: US 8,174,274 B2
(45) Date of Patent: May 8, 2012

(54) NAILER WITH INTEGRATED STUD FINDER

(75) Inventors: Bobby Lynn Lawrence, Palmetto, FL (US); Gregory A. Kramer, Cincinnati, OH (US)

(73) Assignee: Campbell Hausfeld/Scott Fetzer Company, Harrison, OH (US)

( * ) Notice: Subject to any disclaimer, the term of this patent is extended or adjusted under 35 U.S.C. 154(b) by 295 days.

(21) Appl. No.: 12/646,029

(22) Filed: Dec. 23, 2009

(65) Prior Publication Data
US 2011/0148437 A1    Jun. 23, 2011

(51) Int. Cl.
*G01R 27/26* (2006.01)
*B25B 23/145* (2006.01)
*B27F 7/17* (2006.01)
(52) U.S. Cl. .................. 324/686; 173/20; 173/21; 227/5
(58) Field of Classification Search .......................... None
See application file for complete search history.

(56) References Cited

U.S. PATENT DOCUMENTS

| | | | | |
|---|---|---|---|---|
| 4,099,118 A * | 7/1978 | Franklin et al. | ................ | 324/671 |
| 4,464,622 A * | 8/1984 | Franklin | .......................... | 324/67 |
| 5,512,834 A * | 4/1996 | McEwan | ....................... | 324/642 |
| 5,562,240 A * | 10/1996 | Campbell | ....................... | 227/130 |
| 6,188,228 B1 * | 2/2001 | Philipp | .......................... | 324/658 |
| 6,851,487 B1 | 2/2005 | Shotey | | |
| 7,066,278 B2 | 6/2006 | Shotey | | |
| 7,073,268 B1 * | 7/2006 | Etter et al. | ....................... | 33/286 |

* cited by examiner

*Primary Examiner* — Paresh Patel
(74) *Attorney, Agent, or Firm* — Jones Day

(57) ABSTRACT

A nailer incorporates an integrated stud finder for sensing when a stud is present. The nailer has a work contact element and a magazine for storing nails. The stud finder includes a sensor plate coupled to the work contact element of a nailer and a stud sensing circuit coupled to the sensor plate. The stud sensing circuit is provided for reading a capacitance level and for determining whether the sensor plate is positioned adjacent a stud based upon the capacitance level that is read. The stud finder also includes at least one signaling device coupled to the sensor plate for signaling to a user when a stud is present. The sensor plate is coupled to a no mar tip that is tethered to the nailer. A storage post for storing the no mar tip is positioned on the magazine for storing the no mar tip when not in use.

14 Claims, 8 Drawing Sheets

NAILER WITH INTEGRATED STUD FINDER

FIELD

This technology relates to a nail gun or nailer for use in accelerating the nailing process. In particular, the nail gun or nailer incorporates a stud finder to assist in locating a stud.

BACKGROUND

Nail guns or power nailers are known in the home improvement industry and are useful for accelerating the nailing process. The most common power nailers are pneumatic nailers, which are powered by air pressure from a compressor. When a nail is fired, a valve opens in the tool and compressed air fills a cylinder. A piston in the cylinder moves rapidly, driving a nail in front of it into the material at the tip of the nailer. When the piston fully extends, the air from the compressor is released from the tool through an exhaust vent. The piston recoils while another nail is loaded. Another type of Nailer is a cordless nailer, which is similar to a pneumatic nailer but uses a flammable gas, instead of air, to drive the nail.

Power nailers can be used in virtually any type of construction. Some models are designed for use in tight spaces, while others are large and powerful for high demand applications. Framing nailers are designed for fast high-powered work in fastening large pieces of material. Finish nailers are lighter weight, used for furniture, cabinets, trim and molding. Staplers, tackers and brad nailers are also lightweight, used for precision work. Roofing nailers are specifically designed to apply roof shingles.

Two basic types of nailers are widely used today. They vary based on their magazine style and the nails they use. Stick style nailers use nails that are collated, or held together, by strips of paper, plastic or thin wire. These nails form a long slender "stick" that slides into an oblong magazine on the tool. Nails sticks typically vary in length from 20-100 or more nails. Coil style nailers use long, flexible strings of nails joined with wires. The nails are stored in a round magazine on the tool. The magazine rolls the string of nails, allowing as many as 300 nails to be loaded at a time.

Stud finders have been used to identify the location of studs and joists behind drywall. Nails are preferably inserted into studs instead of into drywall alone in order to provide better support for the article being nailed or hung from the nail.

Stud finders are typically hand-held, box-like units that use changes in capacitance to sense the location of a stud within a wall. When the plate inside the stud finder is positioned over drywall, it will sense one dielectric constant, but when it is over a stud, the dielectric constant is different. It works on a capacitance differential generated by density difference. The circuit in the stud finder can sense the change and reports it on its display. Stud finding circuits are known in the art.

Stud finders are typically calibrated at a location on the wall where the user knows that a stud is not present. In order to calibrate the stud finder, the user places the stud finder against the drywall and senses a wall density, which is registered internally within the device as a capacitance. When a stud is not present, the density will be lower and a capacitance reading that is taken by the stud finder will be lower. Once a stud finder is calibrated at a non-stud location, the stud finder may be slid across a wall until it encounters an area of higher density. The area of high density represents the location of a stud, which the stud finder will identify by a higher capacitance reading. Once a stud has been located, the stud finder sends a signal to a user.

Typical signals that are used by stud finders include LED lights and noise, such as a beeping noise. For example, some stud finders will register a green LED color when no stud is present and a red LED color when a stud is present. Some stud finders will beep at a slower pace until they encounter a stud, at which point the beeping will increase in speed. Other signaling techniques, or a combination of the above, have also been used. Once a stud has been located, the user can nail directly into a stud.

BRIEF DESCRIPTION OF THE DRAWING FIGURES

DETAILED DESCRIPTION

Figure 5:
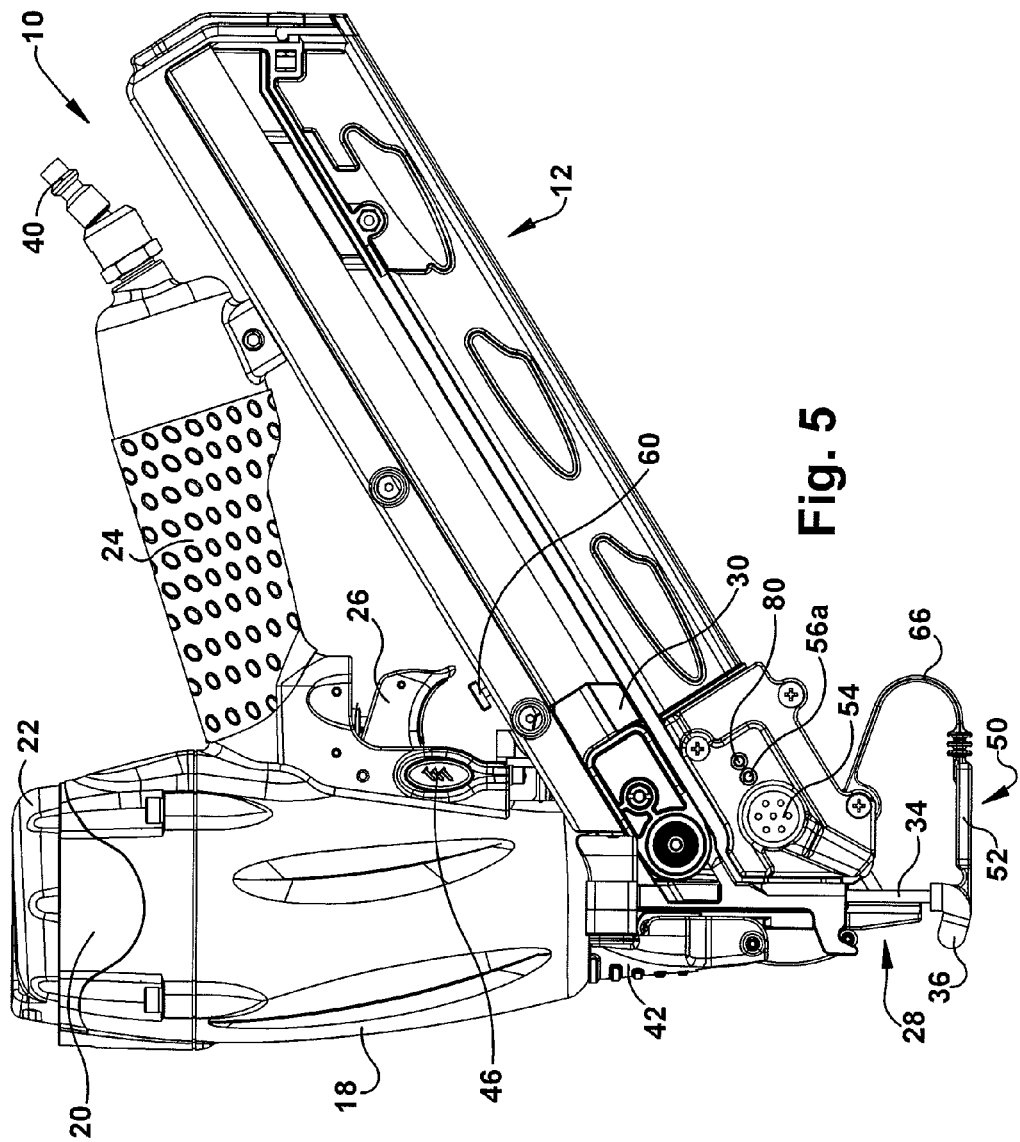
FIG. 5 is a left side view of an alternative example nailer incorporating a stud finder.
Figure 6:
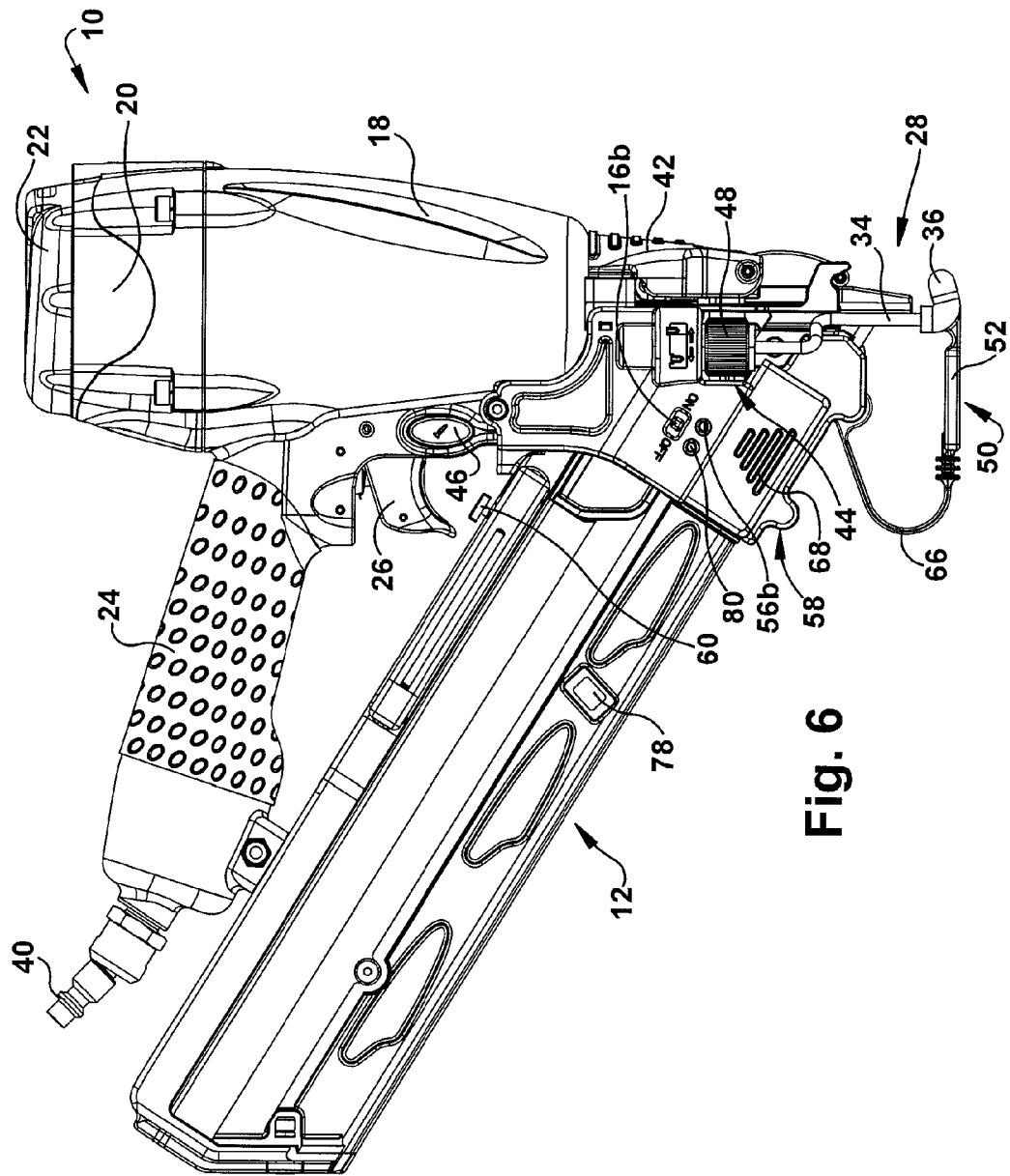
FIG. 6 is a right side view of the example nailer of FIG. 5.

The example nailer 10 is shown in two different embodiments in FIGS. 1-4 and 5-6, respectively. The components included in each example nailer 10 are very similar, with one major difference between the nailers being that the nailer 10 shown in FIGS. 1-4 is a straight finish nailer while the example shown in FIGS. 5-6 is an angle finish nailer. The angle finish nailer 10 has an angled magazine 12 while the straight finish nailer 10 has a straight magazine 14 for holding nails.

Each nailer 10 incorporates similar features. In particular, each nailer 10 includes a power switch 16a, 16b, a head 18, a head cap 20, an exhaust deflector 22, a grip 24, a trigger 26, a nose 28, a magazine 12, 14, a nail pusher 30 that is coupled to the magazine 12, 14 and is utilized to push nails toward the nose 28, a work contact element 34, and a no mar tip 36. A no mar tip 36 is a part that is attached to the work contact element 34 and is utilized to prevent marring of the surface against which the work contact element 34 is pressed. The nailer 10 may be used with or without the no mar tip 36. Each nailer 10 also includes an quick connect inlet plug 40, which is coupled to the grip 24. The quick connect inlet plug 40 is used to couple nailer 10 to a compressor (not shown) in order to pneumatically operate the nailer 10.

The power switch is used to power only the electrical components on the tool. The power switch 16a in the device 10 shown in FIGS. 1-4 is located at the rear of the grip 24 and is turned on by a user gripping the grip 24. This power switch 16a is a tactile switch. The power switch 16a in FIGS. 1-4 includes a 10 second off delay in order to avoid having the user accidentally deactivate the tool 10k through intermittent or short durations, such as while the user repositions the tool in his or her hand. The device shown in FIGS. 5-6 includes a sliding power switch 16b that is positioned adjacent the magazine 12 near the nose 28 of the device 10. With this power switch 16b, the user must slide the button into the on position. The power switch 16a, 16b is utilized to operate the electronic features of the example nailer 10. The power switch 16a, 16b must be "on" in order for the electronic features, including the below described stud finder feature, to operate properly.

Each nailer 10 also incorporates several additional accessory features, including a quick clear nose cover 42 for quickly clearing nails that have become jammed in the nose 28, an adjustable depth control system 44, and a trigger mode switch 46. The adjustable depth control system 44 includes a knurled knob 48 that may be turned in order to increase or decrease the depth of nail insertion. The trigger mode switch 46 allows the user to switch triggering modes.

In typical operation, the no mar tip 36 is pressed against a surface at a location where nailing is desired. The work contact element 34 is a wire element that serves as a safety for the nailer and must be pressed inward in order to allow the nailer to file a nail. The safety is released by pressing the no mar tip 36 and work contact element 34 against the surface. Once the work contact element 34 is depressed, the nailer 10 is operational and the user may pull the trigger 26 in order to fire a nail into a desired surface. These features are known to those of skill in the art.

Each nailer 10 also incorporates an example integral stud finder 50. The stud finder 50 is used to reliably drive a nail through a piece of trim securely into the stud behind the drywall. The stud finder 50 includes a sensor plate 52, a speaker 54, two LED indicators 56, a battery compartment 58, and a stud finder operation switch 60. The LEDs 56, speaker 54, battery compartment 58 and sensor plate 52 are all coupled to a pair of printed circuit boards 62, 64. These features are shown schematically in FIG. 7 and are identified, where applicable, on FIGS. 1-6.

Figure 8:
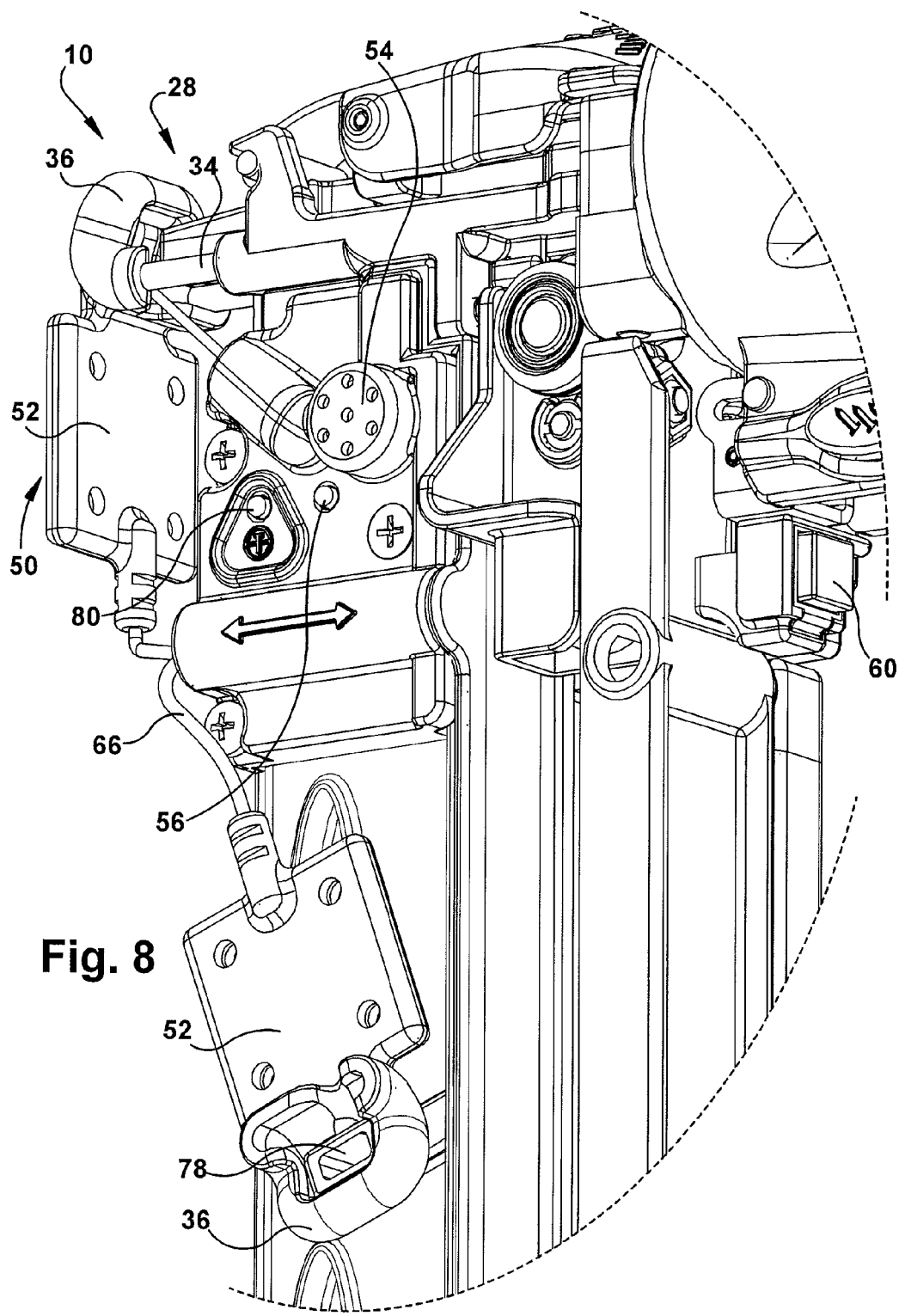
FIG. 8 is an enlarged view of the left side components of the example nailer shown in FIG. 1.

The sensor plate 52 is coupled to the no mar tip 36. The connection between the no mar tip 36 and the sensor plate 52 is preferably rigid so that the no mar tip 36 and sensor plate 52 remain in substantially the same plane as the work contact element 34. The no mar tip 36 has a depth that is minimal such that the no mar tip 36 lies in substantially the same plane as the work contact element 34. The sensor plate 52 is electrically coupled to one of the circuit boards 62 via a single wire tether 66. As shown, the sensor plate 52 is coupled to the left circuit board 62. The single wire serves as a tether 66 for the no mar tip 36/sensor plate 52 such that if the no mar tip 36 is removed from the work contact element 34, the part is not easily lost. If desired, the tether 66 may be retractable so that the no mar tip 36 can be more easily removed from the work contact element 34 and to allow the tether to be positioned on the storage post 78, as shown in FIG. 8. The tether 66 shown in FIGS. 1-4 is retractable by about ¾ inches, although other ranges of retractability may be used based upon the overall position of the various parts. The tether 66 is spring loaded within the nose 28 of the nailer 10. The tether 66 shown in FIGS. 5-6 is not retractable and must have sufficient length to allow the no mar tip 36 to be removed from the work contact element 34 and replaced on the storage post 78.

Figure 1:
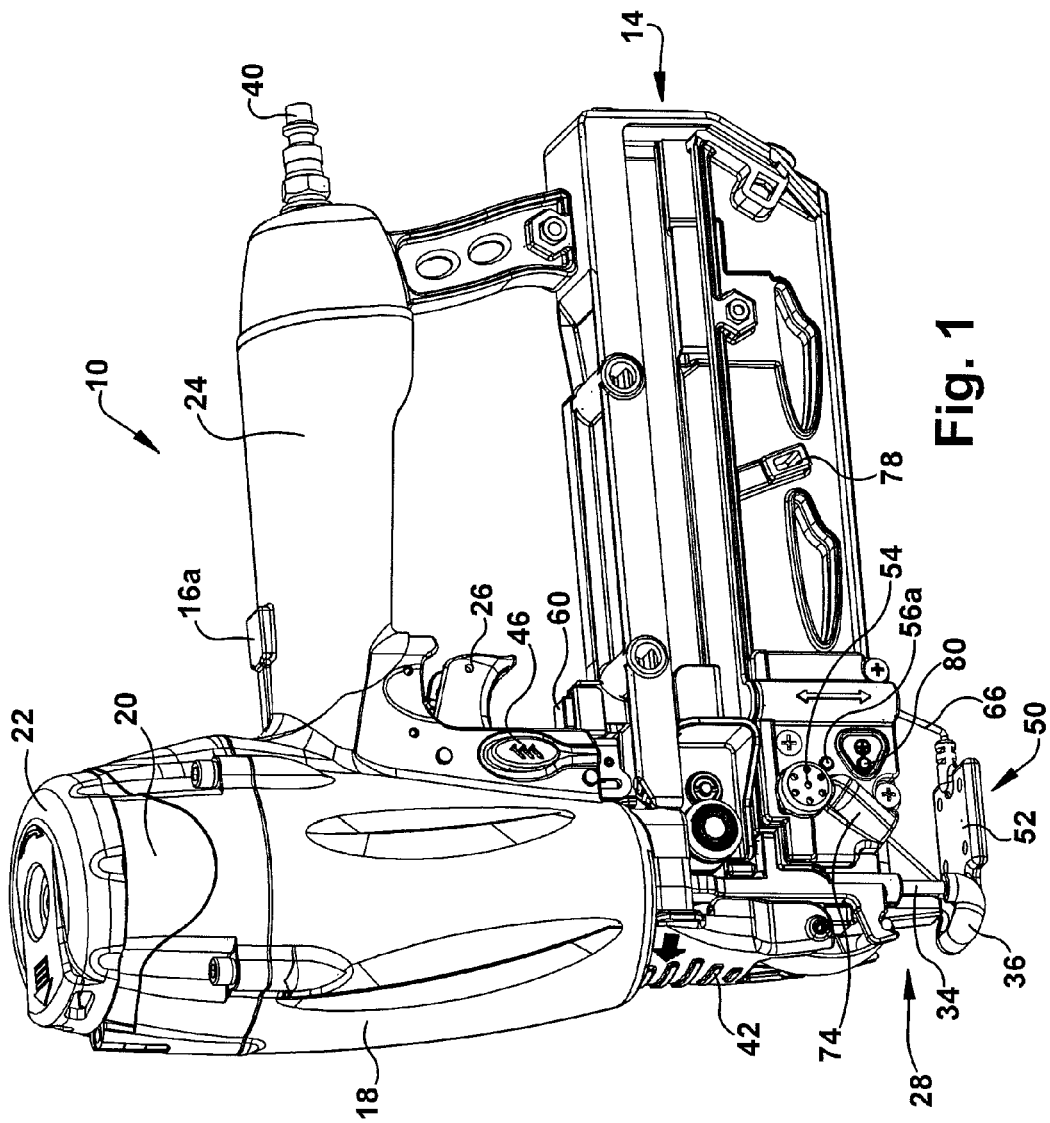
FIG. 1 is a left side view of an example nailer incorporating a stud finder.
Figure 2:
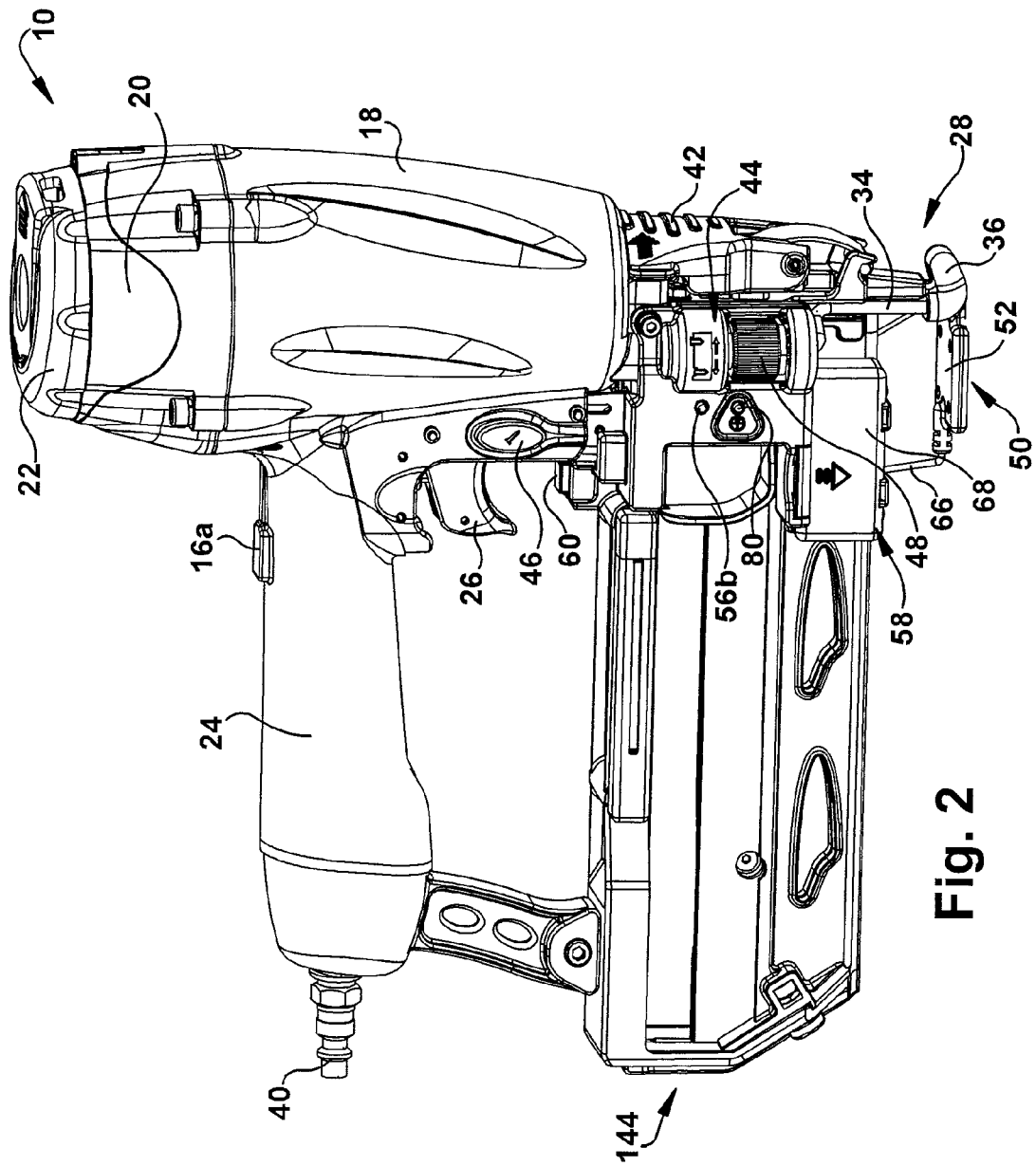
FIG. 2 is a right side view of the example nailer of FIG. 1.
Figure 3:
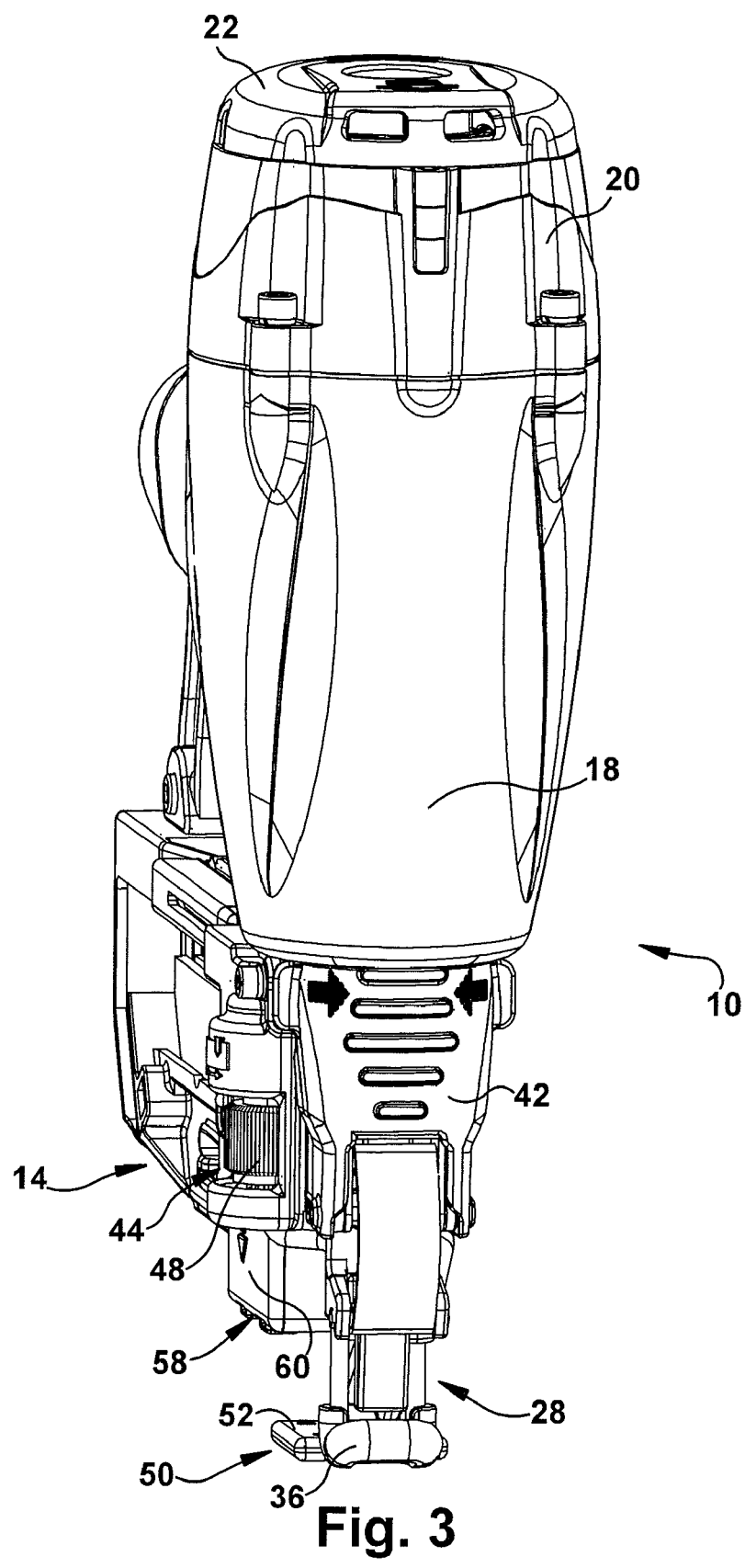
FIG. 3 is a front view of the example nailer of FIG. 1.
Figure 4:
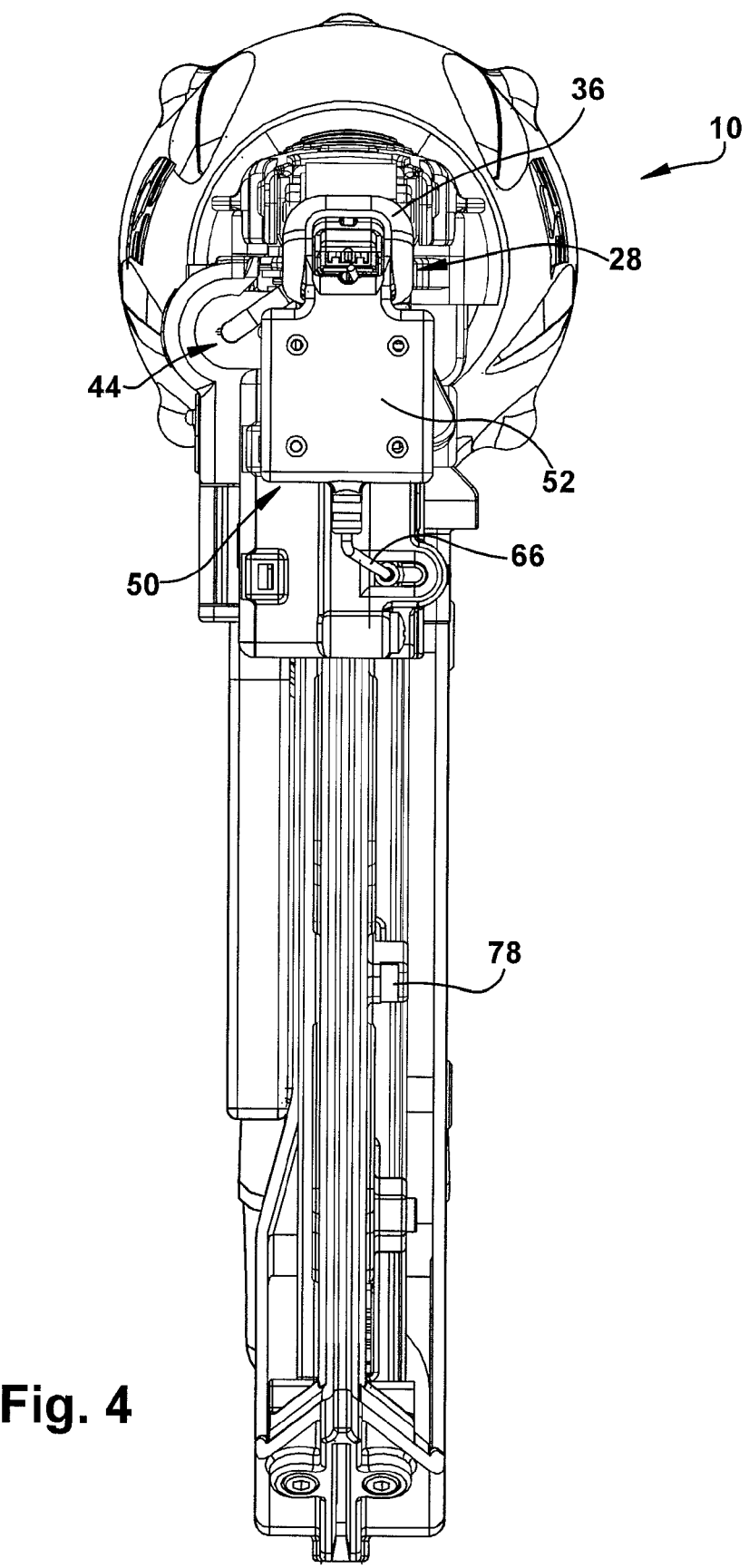
FIG. 4 is a bottom view of the example nailer of FIG. 1.

The battery compartment 58 is utilized to store two AAA batteries, although other power sources may also be utilized. The battery compartment 58 includes a cover 68, as shown in FIGS. 2 and 6, that is slidable over the compartment to contain the batteries 70 in the compartment. The cover 68 is removable to access the batteries 70 for replacement. The cover may be attached by a screw (not shown), if desired. The batteries 70 are used to power the electronics on the nailer 10, including the example stud finder 50. The right circuit board 64 includes two battery power terminals 72 for mating with the batteries 70 at one of their ends. In addition, a spring (not shown) may be utilized to hold each battery 70 in position, as known by those of skill in the art.

A stud sensing circuit is provided for sensing the location of a stud. The stud sensing circuit is a typical stud sensing circuit, as known by those of skill in the art. The circuit operates to sense a capacitance when its powered on. When the sensor plate 52 is positioned against a surface to be nailed and the circuit is turned on, the circuit senses the capacitance in the wall and compares this to a calibrated capacitance level that represents a hollow wall (e.g., no stud). The circuit reacts to changes in capacitance at the sensor plate 52 to signal to a user that a stud has been found via the provided signaling devices/output indicators 54, 56.

The signaling devices have two distinct methods for signaling a user. The speaker 54 emits a beeping noise. When properly calibrated, when a stud is not present, no beeping noise is emitted. As the user approaches a stud, such that the capacitance level starts to increase, the beeping noise will increase in speed. When the sensor plate 52 is finally positioned on top of a stud, the speaker 54 will beep in a rapid or steady fashion. The LEDs 56 are multi-color LEDs and function in a slightly different, but related manner. When the sensor plate 52 is nearing a stud, the LEDs 56 will turn to flashing red. When the sensor plate 52 is positioned over a wall where no stud is present, the LEDs 56 will be lit in a green color. When the sensor plate 52 is positioned over a stud, the LEDs 56 will be lit in a constant red color. Both of the signaling devices 54, 56 signal to a user when a stud is present. While a specific pattern of beeps and flashes are described, other patterns and colors may be used, if desired.

Figure 7:
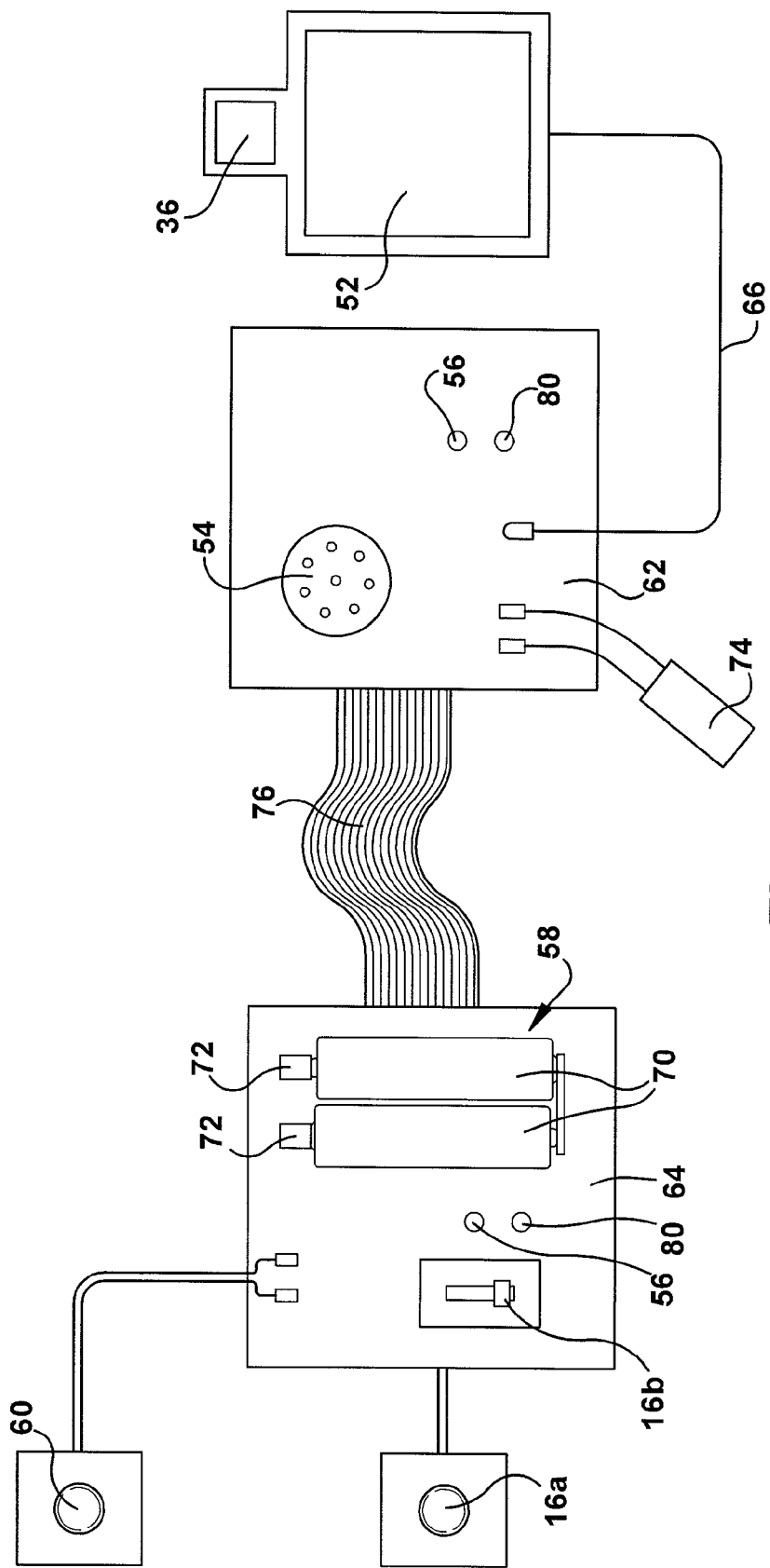
FIG. 7 is a schematic of the electrical components of the stud finder that are incorporated into the example nailer.

A stud finder operation switch 60 is located beneath the trigger 26 and is a push button that the user depresses when stud sensing is desired. The stud finding circuit will only be activated when the button 60 is depressed. In FIG. 7, the stud finder operation switch 60 is coupled to the right side circuit board 64, although it could be coupled to either circuit board. The LEDs 56 include a left side indicator 56a and a right side indicator 56b, with one indicator being coupled to each of the printed circuit boards. A ribbon cable of wires 76 connects the two circuit boards 62, 64 together. In addition, the power switch 16a, 16b is coupled to the right side circuit board 64, although it could be coupled to either circuit board. FIG. 7 shows both power switches 16a, 16b. In use, only one power switch 16a, 16b will be utilized, but both power switches are shown in FIG. 7 for illustration purposes. The speaker 54 is directly mounted on the left side circuit board 62. It could alternatively be mounted to the right side circuit board 64, or a speaker could be positioned on each circuit board.

In addition, other electronic features may also be coupled to the circuit boards that are unrelated to the stud finder operation. For example, a low nail indicator multi-color LED 80 could be coupled to one or both of the circuit boards and a low nail indicator circuit could be utilized to inform the user that the supply of nails in the magazine 12, 14 is low. In addition, a laser placement guide 74 could be coupled to one of the circuit boards 62 for use in providing a laser guide on the device to assist in placement of the nail.

While the batteries 70 are shown installed directly on the circuit board 64, it may be desired to space the batteries 70 from the circuit board 64. This decision could be a function of the location of the circuit board 64 within the housing of the nailer 10 and accessibility of the batteries 70 relative to the circuit board 64. Thus, the batteries 70 may be spaced from the circuit board 64, in which case the battery terminals 72 would be coupled to the circuit board 64 in a conventional manner with leads, solder pads, and the like, as known by those of skill in the art.

In addition, any number of electronics may be coupled to one or both of the circuit boards 62, 64. Only a few components are shown in FIG. 7 for simplicity purposes. However, it should readily be recognized that other components could be coupled to or mounted directly on one or both of the circuit boards 62, 64.

While two circuit boards are shown, a single circuit board could alternatively be utilized. When a single circuit board is used, signaling devices could be separated from the circuit board but coupled to the board via leads or other electronic connectors, or signaling devices could be positioned only on one side of the device. Other techniques for incorporating a single circuit board are also contemplated.

By integrating the stud finder 50 into the nailer 10, the user is no longer required to use two different devices to identify a stud and then nail into the stud. Instead, the user can simply place the sensor plate 52 and no mar tip 36 against a surface, locate a stud, and drive a nail. This results in a significant simplification of the nailing process, as well as a reduction in the number of tools that are necessary. The stud finder 50 is a time-saving feature. Users can now nail with a single step, thereby attracting reliable stud finding to more contractors who bypass this sometimes critical step. Also, the Do-It-Yourself user is less likely to lose the tool.

The stud finder 50 must first be calibrated in order to sense the location of a stud. The calibration technique, as known by those of skill in the art, is as follows. First the user installs batteries 70 into the battery compartment 58. Then the power switch 16a or 16b must be turned on. In the case of the nailer 10 shown in FIGS. 1-4, the power switch 16a at the front of the grip is turned on. In the case of the nailer 10 shown in FIGS. 5-6, the sliding switch 16b near the nose 28 is turned on. The magazine 12, 14 of the nailer 10 is then loaded with nails and the nailer 10 is coupled to an air source, such as a 70 to 120 psi air source.

The device is then calibrated. The user places the sensor plate 52 against a portion of the wall in a location where it is believed that no stud is present. It is not necessary to depress the work contact element 34. All that is needed is for the sensor plate 52 to rest against the wall. Then the user presses and holds in the stud finder operation button 60. This begins the calibration process for the stud finder sensor circuit, which typically takes less than approximately one second. During the calibration process, the speaker 54 will sound a continuous beep and the LEDs 56 will be red continuously. After approximately one second, the sensor circuit is calibrated, the beeping will stop, and the LEDs 56 will turn green continuously. The user may now begin seeking a stud.

The user will typically place a piece of trim in their hand, with the intent that the trim will be nailed to the stud. The user can then move the sensor plate 52 against the wall until the signaling devices/output indicators 54, 56 begin to signal that a stud is detected. The signaling devices do not change until the edge of a stud is detected. When the edge of a stud is detected, the speaker 54 begins beeping continuously. The closer the stud becomes, the faster the beeping will be. The LEDs 56 begin flashing red, on and off, as the stud becomes closer. The closer the stud becomes, the faster the LEDs will flash. When the signal becomes strong enough, representing the center of the stud, the speaker 54 will sound a continuous beep and the LEDs 56 will become continuously red.

Once the stud has been located, the user may release the stud finder operation button 60 and move the nailer 10 into position over the trim and fire the nailer 10 into the trim at the desired location. The user may then move across the wall to locate other stud locations and repeat the steps above until the entire piece of trim has been nailed to the studs.

Once the user is finished nailing, the nailer 10 may be disconnected from the air source, the nails may be unloaded from the magazine 12, 14, and the power switch 16a, 16b should be turned to the off position. The batteries 70 may be removed for long term storage.

Referring to FIG. 8, if during use the user decides to remove the no mar tip 36 (in order to position the work contact element 34 closer to the surface, for example), the no mar tip 36 and sensor plate 52 may be conveniently stored on the storage post 78 that extends outwardly from the magazine. The no mar tip 36 is shown positioned in the two different possible storage positions in FIG. 8. In one position, the no mar tip 36 is positioned on the work contact element 34. In a second position, the no mar tip 36 swings downwardly on the tether and is coupled to the storage post 78. The storage post 78 may be molded with the material of the magazine 12, 14 during production. Alternatively, the storage post 78 could be attached with a fastener, such as a screw, to the magazine. Because the sensor plate 52 is tethered to the device, the post 78 must be positioned in a location that will allow the sensor plate 52 to continue to be tethered, taking into account the retractability of the tether 66.

As shown in FIG. 7, one wire lead 90 is utilized in the sensor plate 52. Alternatively, more than one wire lead could be utilized. To the extent that a sensor plate 52 is described herein, it shall include one wire lead or multiple wire leads. The sensor plate 52 itself may be removed and the wire lead(s) could be included in the no mar tip 36. Thus, sensor plate 52 also includes within its definition a unit that does not include a separate sensor plate 52, but instead incorporates the features of a sensor plate 52 into the no mar tip 36. The sensor leads preferably do not contact the work contact element 34.

The nailer 10 may also include additional features, such as a laser placement guide 74, which helps the user to specifically identify where the nail will be driven with the assistance of a laser. The nailer 10 may incorporate a bubble level to assist the user in maintaining the device in a horizontal or vertical position. The level can be positioned at any location on the device, as desired. The device may incorporate a mode change switch 46 for changing the tool from bump mode to sequential, or other modes. The device may incorporate a low nail indicator 80, which signals to the user when the nailer 10 has fewer than 10 or 5 nails. A signal is displayed to tell the user that 10 or fewer nails are present and a different signal is displayed to tell the user that 5 or fewer nails are present in the magazine.

The examples described herein can be used with any type of nailer. One particularly useful application is the finish nailer. Alternatively, the above-described examples could also be used with another power tool, such as a driver, a drill, a screwdriver, or the like.

The term "substantially" if used herein is a term of estimation.

While various features of the claimed invention are presented above, it should be understood that the features may be used singly or in any combination thereof. Therefore, the claimed invention is not to be limited to only the specific embodiments depicted herein.

Further, it should be understood that variations and modifications may occur to those skilled in the art to which the claimed invention pertains. The embodiments described herein are exemplary of the claimed invention. The disclosure may enable those skilled in the art to make and use embodiments having alternative elements that likewise correspond to the elements of the invention recited in the claims. The intended scope of the invention may thus include other embodiments that do not differ or that insubstantially differ from the literal language of the claims. The scope of the present invention is accordingly defined as set forth in the appended claims.

What is claimed is:

1. A stud finder for a nailer having a work contact element and a magazine for storing nails comprising:
    a sensor plate coupled to a work contact element of a nailer to move with the work contact element into and out of contact with a work surface and, when in contact with the work surface, to move with the work contact element relative to the nailer upon depression of the work contact element inward of the nailer;
    a stud sensing circuit coupled to the sensor plate for reading a capacitance level and for determining whether the sensor plate is positioned adjacent a stud based upon the capacitance level that is read; and
    at least one signaling device coupled to the sensor plate for signaling to a user when a stud is present.

2. The stud finder of claim 1, wherein the sensor plate is coupled to a no mar tip that is configured to seat on the work contact element.

3. The stud finder of claim 2, wherein the no mar tip is removable from the work contact element and further comprising a storage post positioned on a magazine of the nailer for holding the no mar tip and sensor plate in an uninstalled position.

4. The stud finder of claim 1 wherein the sensor plate is detachably coupled to the work contact element, and further comprising a tether attaching the sensor plate to the nailer at a location remote from the work contact element.

5. The stud finder of claim 4 wherein the tether is spring loaded for retraction inward of the nailer.

6. The stud finder of claim 4 wherein the tether includes electrical wiring coupling the sensor plate with a capacitance sensing circuit on the nailer.

7. The stud finder of claim 4 further comprising a no mar tip detachably coupling the sensor plate to the work contact element.

8. The stud finder of claim 7 wherein the sensor plate is rigidly coupled to the no mar tip.

9. The stud finder of claim 4 further comprising means for detachably coupling the sensor plate to the nailer at second location remote from the work contact element when the sensor plate is detached from the work contact element.

10. The stud finder of claim 9 wherein the means for detachably coupling the sensor plate to the nailer comprises an aperture receiveable over a post.

11. A stud finder for a nailer having a work contact element and a magazine comprising:
    a no mar tip coupled to the work contact element and removable therefrom;
    a sensor plate coupled to the no mar tip for removal from the work contact element with the no mar tip;
    a stud sensing circuit coupled between the sensor plate and the nailer; and
    a post coupled to the magazine, wherein the post is sized to hold the no mar tip and sensor plate in position thereon when the no mar tip is removed from the work contact element.

12. The stud finder of claim 11, wherein the sensor plate is rigidly coupled to the no mar tip.

13. The stud finder of claim 11, wherein the no mar tip is tethered to the nailer via a tether.

14. The stud finder of claim 13, wherein the tether is retractable.

* * * * *